United States Patent [19]
Kayan et al.

[11] Patent Number: 5,324,270
[45] Date of Patent: Jun. 28, 1994

[54] CANNULA WITH IMPROVED VALVE AND SKIN SEAL

[75] Inventors: Helmuth L. Kayan, Redwood City; Kenneth H. Mollenauer, Santa Clara, both of Calif.

[73] Assignee: General Surgical Innovations, Inc., Portola Valley, Calif.

[21] Appl. No.: 968,201

[22] Filed: Oct. 29, 1992

[51] Int. Cl.$^5$ .............................................. A61M 5/00
[52] U.S. Cl. ................................. 604/167; 137/847; 251/149.3
[58] Field of Search ................ 606/185; 604/167, 169; 137/847, 850, 846; 251/149.3, 149.6

[56] References Cited

U.S. PATENT DOCUMENTS

| | | | |
|---|---|---|---|
| 2,526,629 | 10/1950 | Bourke | 137/847 |
| 3,566,964 | 3/1971 | Livingston | 137/847 |
| 4,419,094 | 12/1983 | Patel | 604/93 |
| 4,917,668 | 4/1990 | Haindl | 604/167 |
| 5,009,643 | 4/1991 | Reich et al. | 606/185 |

FOREIGN PATENT DOCUMENTS 3042229  5/1982  Fed. Rep. of Germany ...... 604/167

Primary Examiner—Tamara L. Graysay
Attorney, Agent, or Firm—Flehr, Hohbach, Test, Albritton & Herbert

[57] ABSTRACT

A cannula having an elongate rigid tubular member with proximal and distal extremities. A cylindrical housing is secured to the proximal extremity of the tubular member. A duckbill valve assembly is disposed in the cylindrical housing. The valve assembly has a valve member formed of an elastomeric material and having first and second leaflets forming a duckbill-type seal. First and second spring fingers are provided which engage said first and second leaflets and yieldably urge the leaflets into a closed position whereby in the event the leaflets take a permanent set towards an open position, the spring fingers will urge the first and second leaflets into a closed sealing position.

6 Claims, 2 Drawing Sheets

CANNULA WITH IMPROVED VALVE AND SKIN SEAL

This invention relates to a cannula with improved valve and skin seal.

Cannulas have heretofore been provided. Typically they have utilized a flapper-type valve. It has been found that this flapper-type valve is unsatisfactory where large devices are inserted through the cannula and particularly where it is necessary to shift the cannula with the devices disposed therein. In addition, in such cannulas, it has been found that the skin seals provided have made it difficult to adjust the depth of penetration of the cannula. There is therefore a need for a new and improved cannula which overcomes these disadvantages.

In general, it is an object of the present invention to provide a cannula with an improved valve which will always move to a closed position when a device inserted through the cannula is removed for of period of time.

Another object of the invention is to provide a cannula of the above character in which a duckbill valve is utilized and in which additional means is provided for ensuring that the duckbill valve will always return to a closed sealing position even though the duckbill valve takes a permanent set because of a device being inserted through the cannula and being left therein for a period of time.

Another object of the invention is to provide a cannula of the above character in which resilient spring fingers are utilized for ensuring that the duckbill valve returns to a closed or sealed position when a device is removed from the cannula.

Another object of the invention is to provide a cannula of the above character in which the depth of penetration of the cannula can be readily adjusted.

Another object of the invention is to provide a cannula of the above character in which the cannula is provided with a skin seal which can be readily moved between released and engaged positions by the use of the same hand engaging the cannula.

Another object of the invention is to provide a cannula of the above character in which the depth of penetration of the cannula can be adjusted by a single hand.

Additional objects and features of the invention will appear from the following description in which the preferred embodiments are set forth in detail in conjunction with the accompanying drawings.

In general the cannula with improved valve and skin seal incorporating the present invention consist of an elongate rigid tubular member having proximal and distal extremities. A cylindrical housing is secured to the proximal extremity of the tubular member. A valve member formed of an elastomeric material is provided and has first and second leaflets forming a duckbill valve. Means is provided which includes first and second spring fingers formed of a spring metal engaging the first and second leaflets and yieldably urging said leaflets into a closed position regardless of whether a permanent set has formed in the leaflets. The skin seal is comprised of a first tubular member slidably mounted on the elongate tubular member. The first tubular member has a cylindrical bore and is provided with a radially extending flange with a finger engaging surface formed thereon to facilitate rotation of the first tubular member. A resilient grasping member is disposed in the cylindrical recess. Releasable means movable between released and engaged positions is carried by the first tubular member for moving the grasping member between gripping and non-gripping positions with respect to the elongate tubular member. The releasable means is engagable by the fingers of the same hand grasping the cannula so that when said releasable means is in a released position said first tubular member can be moved longitudinally of the elongate tubular member and in engaged position prevents shifting of the first tubular member relative to the elongate tubular member.

More in particular, the cannula 11 incorporating the present invention consists of an elongate rigid tubular member 12 formed of a suitable plastic material such as polycarbonate. The tubular member 12 can have a suitable length as for example approximately 11 centimeters with an outside diameter of 12 millimeters and the inside diameters of 11 millimeters to provide a wall thickness of approximately 0.5 millimeter. The elongate tubular member 12 has proximal and distal extremities 13 and 14 and has a flow passage 16 extending therethrough.

Figure 2:
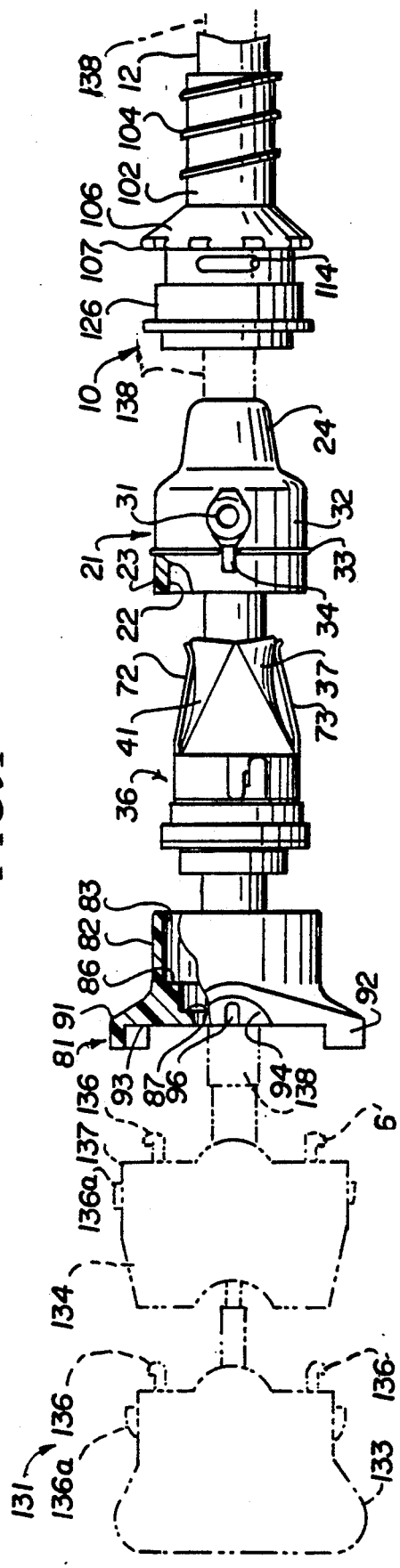
FIG. 2 is a view similar to FIG. 1 but showing the cannula in an exploded form.

A cylindrical housing 21 is provided formed of a suitable plastic material such as polyvinylchloride. It has a suitable length as for example 4 centimeters and has a suitable outside diameter as for example 2.5 centimeters with a wall thickness of 1 millimeter to provide a cylindrical recess 22 therein which is open at one end. The housing 21 has proximal and distal extremities 23 and 24. The distal extremity 24 is tapered as shown and is provided with a bore 26 which terminates in an annular lip 27 formed as a part of the housing 21 which opens into the cylindrical recess 22 in the housing 21. The proximal extremity 13 of the elongate tubular member 12 is disposed within the bore 26 and abuts the lip 27 and is retained therein by suitable means such as an adhesive (not shown). A male Luer fitting 31 is provided on the side wall 32 of the housing 21 forming the cylindrical recess 22. An outwardly standing flange 33 is provided on the exterior surface of the wall of the housing 21 adjacent the proximal extremity for a purpose hereinafter described. A raised rectangular protrusion 34 is formed on the exterior surface of the wall 32 and has the distal extremity in alignment with the distal edge of the flange 33 (see FIG. 2).

A cylindrical duckbill valve assembly 36 forming the improved valve means is disposed within the cylindrical recess or chamber 22 of the housing 21 and consists of a valve member 37 formed of a suitable medical grade elastomeric material. The valve member 37 is provided with proximal and distal extremities 38 and 39. The valve member 37 consists of duckbill-like leaflets 41 and 42 which are inclined inwardly and distally towards each other at a substantial angle to form a seal 43 extending diametrically across the valve member 37. The leaflets 41 and 42 are formed integral with a cylindrical portion 46 of the valve member 37 which adjoins another cylindrical portion 47. The cylindrical portion 47 adjoins a radially-extending flange 48. The angles of the leaflets 41 and 42 have been selected so that they are relatively steep, as for example less than 45° from the longitudinal axis of the duckbill valve assembly 36. This ensures that the distal lens face of an endoscope inserted through the cannula 11 and the duckbill valve assembly 36 will not come into contact with the leaflets. This ensures that the lens will remain clean and free of debris which could distort the images produced by the endoscope.

Figure 3:
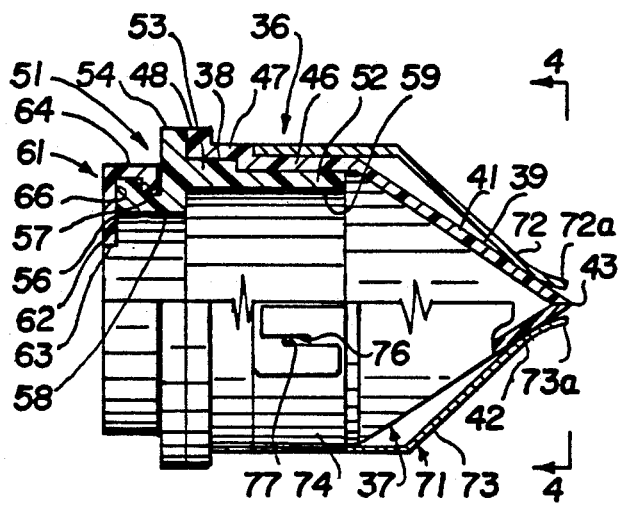
FIG. 3 is a side elevational view partially in cross-section of the improved valve in the form of a duckbill assembly shown in FIG. 2.
Figure 4:
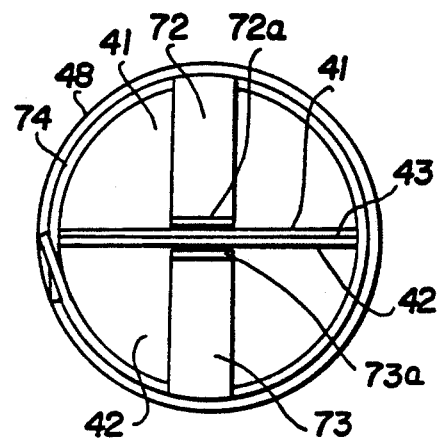
FIG. 4 is an end view looking along the line 4—4 of FIG. 3.
Figure 6:
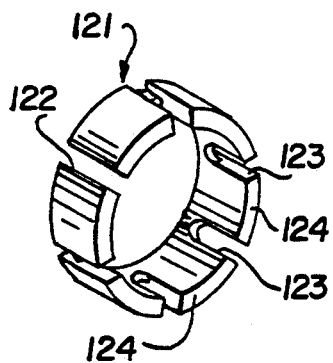
FIG. 6 is an isometric view of the collet utilized in the skin seal shown in FIG. 5.

As can be seen from FIG. 3, the proximal extremity 38 of the valve member 37 is fitted over an insert 51 formed of a suitable material such as a rigid plastic. The insert 51 is provided with a cylindrical portion 52 over which the cylindrical portion 46 of the valve member 37 fits. It is also provided with a cylindrical portion 53 over which the cylindrical portion 47 of the valve member 37 fits. It is also provided with a radially-extending flange 54 and an upstanding portion 56 which has an annular recess 57 therein. The insert 51 is provided with a bore 58 which extends through the portion 56 and which opens into a larger bore 59 extending through the portions 52 and 53.

A second or additional valve member 61 is provided which is also formed of a medical grade elastomeric material. The valve member 61 is formed with a planar wall 62 which has a centrally disposed opening 63 therein which is adapted to form a ring seal as hereinafter described. The valve member 61 is also provided with a cylindrical wall 64 which adjoins the wall 62 at a right angle. The wall 64 is provided with an annular recess 66 underlying the wall 62 which receives the upstanding portion 56 of the insert 51.

Spring means 71 is provided forming a part of the duckbill assembly 36 to ensure that the leaflets 41 and 42 are always yieldably urged towards a closed sealing position to form the seal 43 even though a permanent set may have taken place with respect to the leaflets 41 and 42 by reason of having a device extending therethrough for a substantial period of time as hereinafter described. Such spring means 71 includes first and second flat spring members 72 and 73 which are formed integral with and extending distally from a band 74. The band 74 and the flat spring members 72 and 73 are formed of a suitable material such as stainless steel. The ends of the band 74 are provided with retaining means in the form of slots 76 and 77 extending transversely in opposite directions so that the ends of the band can be fastened together as shown in FIG. 3 to circle the cylindrical portion 46 of the valve member 37 and be retained thereon. The spring fingers 72 and 73 are diametrically opposed to each other and are provided with outwardly turned end portions 72a and 73a respectively that yieldably engage the leaflets 41 and 42 in a region adjacent the seal 43 and yieldably urge the leaflets 41 and 42 into a closed or sealing position.

The duckbill valve assembly 36 is adapted to be disposed within the cylindrical recess or chamber 22 with the flange 48 of the valve member 37 being seated on the side wall 32 and retained in engagement therewith by the flange 54 of the insert 51. The duckbill assembly 36 is retained within the housing 21 by a cap 81 formed of a suitable material such as rigid plastic and of the same material as the housing 21. The cap is provided with a cylindrical portion 82 which is provided with a bore 83 and is adapted to fit over the housing 21. The cylindrical portion is also provided an elongate recess 84 extending longitudinally of the cylindrical portion 82 and is adapted to and mate with the protrusion 34 to ensure proper alignment of the cap 81 with the housing 21. The cap 81 is provided with an annular shoulder 86 which is adapted to abut the insert 81 and hold it firmly in engagement with the housing 21. It is also provided with another annular shoulder 87 which is adapted to abut the wall 62 of the valve member 61. Slots 93 are formed in the lobes 91 and 92 which are used for a purpose hereinafter described. Similarly, the cap 81 is provided with diametrically opposed arcuate recesses with slots 96 therein which are also utilized for a purpose hereinafter described.

Figure 5:
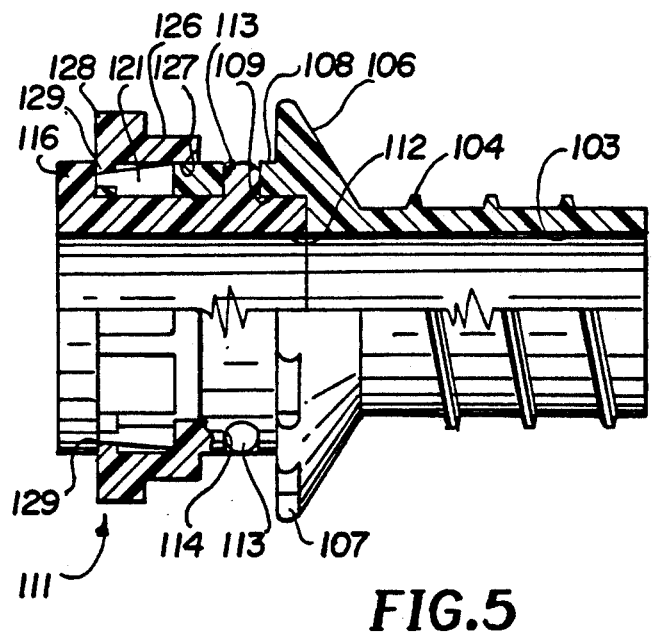
FIG. 5 is a side elevational view of the skin seal for the cannula.

The cannula 11 also includes a skin seal assembly 101 which consists of a screw body 102 formed of a suitable material such as a rigid plastic which is provided with a bore 103 extending therethrough (see FIG. 5) that is adapted to slidably fit over the exterior surface of the elongate tubular member 12 and fixedly engage the same. The body 102 is provided with helical screw threads 104 on the exterior surface of the same. It is also provided with a radially-extending flange 106 which has circumferentially spaced-apart rounded protrusions 107 formed thereon adapted to be engaged by the fingers of a hand for rotation of the screw body 102. The flange 106 is provided with an upstanding cylindrical portion 108 which has a cylindrical wall 109 formed therein.

An insert 111 is provided within the wall and is formed of a suitable resilient material such as silicone. Insert 111 has a bore 112 extending therethrough which is in alignment with bore 103 of the body 102. The insert 111 is provided with diametrically extending ears 113 which are in registration with and extend through slots 114 provided in the upstanding wall portion 108 to retain the insert 111 within the wall 109. The insert 111 is provided with radially-extending flange 116.

A split-ring collet 121 is mounted on the insert 111 below the flange 116. The collet 121 is provided with a slot extending longitudinally thereof. It is also provided with a plurality of circumferentially spaced-apart slots 123 which extend inwardly from one end of the same but do not extend all the way through the collet. Thus by way of example, five of such slots 123 can be provided which extend transversely substantially through the entire width of the collet. The collet is formed so that it has an increasing thickness extending in a direction toward the open end of the slots 123.

A grip ring 126 formed of a suitable material such as plastic is provided and has a bore 127 permitting the grip ring 126 to slidably move over the exterior surface of the wall portion 108 of the screw body 102. It is also provided with a radially-extending flange 128 to facilitate grasping of the grip ring by the fingers of the hand. The grip ring 126 is provided with an inwardly-extending shoulder 129 which is adapted to engage the outer surface of the collet 121. The grip ring 126 is movable towards and away from the flange 106 of the screw body 102 between first and second positions. As it is moved towards the flange 106 to the first position, the shoulder engages the outer inclined surface of the collet 121 and urges the yieldable fingers 124 of the collet inwardly against the resilient insert 111 to force the same into tighter frictional engagement with the elongate tubular member 12 to retain the skin seal assembly at a predetermined location longitudinally of the elongate tubular member 12. In movement of the grip ring 126 away from the flange 106 to the second position, the collet 121 releases the resilient insert 111 to permit longitudinal movement of the tubular member 12 with respect to the skin seal assembly 101.

Operation and use of the cannula 11 in connection with a laparoscopic procedure may now be briefly described as follows. Let it be assumed that the cannula 11 is to be used in conjunction with a tunneling device of the type described in copending application Ser. No. 07/893,988 field on Jun. 2, 1992. As described therein, such a tunneling device 131 consists of a handle 132 having two parts 133 and 134 which each of the parts carrying a pair of latches 136 with finger engagable portions 136a and spaced apart arcuate protrusions 137. The part 134 includes an introducer member 138 through which there extends a tunneling rod 139 secured to the part 133. A rounded tip 141 is provided on the distal extremity of the tunneling rod 139.

Let it be assumed that the cannula 11 has been shipped with a tunneling device 131 extending therethrough. When this is the case, the introducer member 138 extends through the duckbill valve assembly 36 and as shown in particularly in FIG. 2, the duckbill assembly 36 is expanded to its largest dimension. The arcuate protrusions 137 carried by the part 134 are seated within the arcuate recesses 94 provided in the cap 81. Also the latches 136 carried by the part 134 are seated within the slots 93 provided in the cap 81.

Figure 1:
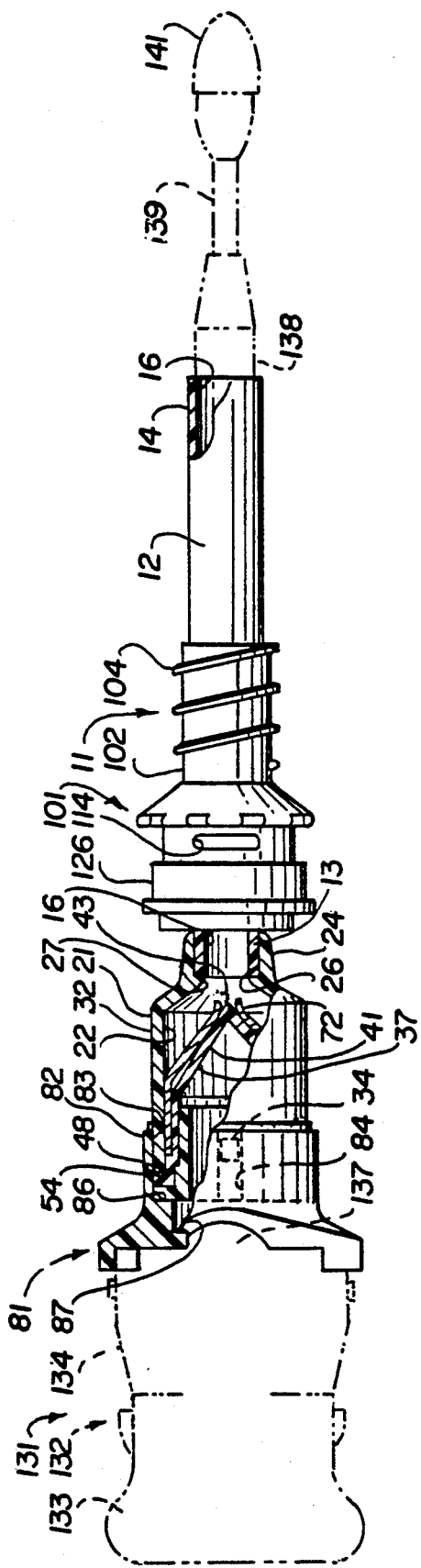
FIG. 1 is a side elevational view of a cannula with improved valve and skin seal incorporating the present invention and as shown in broken lines with a tunnelling device mounted therein.

Assuming that the cannula has been shipped with the tunneling device 131 in the manner shown in FIG. 1, the tunneling device can be removed from the cannula by depressing the portions 136a of the latches 136 carried by the part 134 to permit the tunneling assembly to be pulled out of the cannula 11. The spring fingers 72 and 73 ensure that the duckbill valve 37 returns to a sealed or closed position. The cannula 11 can then be introduced into the appropriate location in the abdomen of the patient as for example in connection with the hernia repair by utilizing a trocar of a conventional type and inserting the same through the cannula to make the opening in the abdominal wall and then pushing the cannula 11 along with the trocar into the abdominal cavity. Then the physician can adjust the depth of penetration of the cannula using the same hand that is holding the cannula to rotate the flange 106 of the screw body 102 by having the thumb and forefinger grasp the protrusions 107 to rotate the screw body 102 into the opening in the abdominal wall formed by the trocar. Thus the body 102 is threaded into the opening by use of the helical screw threads 104. This rotation of the screw body 102 can be accomplished independent of the rotation of the elongate tubular member 12 by lifting or pulling away the grip ring 126 from the flange 106 to permit relative rotation between the screw body 102 and the elongate tubular member 12. After the screw body 102 has been rotated to the desired position, the elongate tubular member 12 can be adjusted longitudinally of the skin seal assembly 101 to the desired depth merely by moving the elongate tubular member 12 inwardly or outwardly with respect to the skin seal assembly 101. After the tubular member 12 is in the desired position, the fingers of the same hand which is causing the longitudinal movement of the elongate tubular member 12 can engage the grip ring 126 to move it towards the flange 106 to a first position and to thereby cause the collet 121 to deform the resilient insert 111 to tightly and frictionally engage the elongate tubular member 12 to prevent further longitudinal movement of the elongate member 12 relative to the skin seal assembly 101. After this has been accomplished, the tunneling device 131 can then be introduced through the cannula 11 and through the ring seal 63 formed by the valve member 61 for one seal and through the duckbill valve assembly 36 for another seal, and operations performed as described in copending application Ser. No. 07/893,988 filed on Jun. 2, 1992.

From the foregoing it can be seen that there has been provided a cannula which is provided with a skin seal assembly 101 which permits adjustment of the cannula with respect to the skin seal assembly by the physician using a single hand. In addition, the cannula has been provided with a duckbill valve assembly which makes it possible to accommodate large diameter medical devices as for example the tunneling device hereinbefore described. The resilient spring metal fingers provided as a part of the duckbill valve assembly serve to ensure that the leaflets of the duckbill valve assembly will always return to a closed position even though the duckbill leaflets may have a tendency to take a permanent set when they are held in an open position by a device being retained within the cannula for long periods of time as for example between shipment and use of the device by a physician.

What is claimed is:

1. In a cannula, an elongate rigid tubular member having proximal and distal extremities, a cylindrical housing secured to the proximal extremity of the tubular member and a duckbill valve assembly disposed in the cylindrical housing, said valve assembly having a valve member formed of an elastomeric material and having first and second leaflets forming a duckbill seal extending diametrically across the valve member, a band encircling the valve member, the band having two ends, means at each end for retaining the band on the valve member first and second spring fingers formed integral with the band and extending distally from the band, said first and second spring fingers engaging said first and second leaflets and yieldably urging said leaflets into a closed position whereby in the event the leaflets take a permanent set towards an open position, the spring fingers will overcome the permanent set and urge the first and second leaflets into a closed sealing position.

2. In a cannula, an elongate rigid tubular member having proximal and distal extremities, a cylindrical housing secured to the proximal extremity of the tubular member and a duckbill valve assembly disposed in the cylindrical housing, said valve assembly having a valve member formed of an elastomeric material and having first and second leaflets forming a duckbill seal, first and second spring fingers engaging said first and second leaflets and yieldably urging said leaflets into a closed position whereby in the event the leaflets take a permanent set towards an open position, the spring fingers will overcome the permanent set and urge the first and second leaflets into a closed sealing position, a skin seal assembly slidably mounted on said elongate tubular member, said skin seal assembly having a body slidably mounted on said elongate tubular member, said body having a bore extending therethrough through which the flexible elongate member extends, an insert formed of resilient material carried by said body and having a bore therein in registration with the bore in the body and having the elongate member extend therethrough, a collet mounted on said insert and a grip ring movable between first and second positions and in the first position engaging said collet to move said collet in a direction to move said resilient means into frictional engagement with the elongate tubular member to prevent longitudinal movement of the elongate member relative to the resilient insert and in the second position permitting the elongate member to be slidably moved within the insert.

3. A cannula as in claim 1 wherein said spring fingers extend in a direction longitudinal of the leaflets of the valve member.

4. In a cannula, an elongate rigid tubular member having proximal and distal extremities, a cylindrical housing secured to the proximal extremity of the tubular member and a duckbill valve assembly disposed in the cylindrical housing, said duckbill valve assembly having a valve member formed of an elastomeric material and having first and second leaflets forming a duckbill seal, first and second spring fingers engaging said first and second leaflets and yieldably urging said leaflets into a closed position whereby in the event the leaflets take a permanent set towards an open position, the spring fingers will overcome the permanent set and urge the first and second leaflets into a closed sealing position, said duckbill valve assembly including a cylindrical insert of a rigid material having a passage extending therethrough and having a radially-extending flange intermediate the ends of the cylindrical insert, said valve member having a cylindrical portion engaging said cylindrical insert and having a flange underlying in juxtaposition to the flange of the insert and an additional valve member formed of an elastomeric material secured to said insert and having a radially-extending wall with an opening therein which is adapted to form a circular seal with respect to a device inserted therethrough.

5. In a cannula, an elongate rigid tubular member having proximal and distal extremities, a housing secured to the proximal extremity of the elongate tubular member, valve means disposed within the housing, a skin seal assembly slidably mounted on the elongate tubular member, said skin seal assembly comprising a body having a bore extending therethrough and through which the elongate member extends, an insert formed of resilient material carried by the body and having a bore therein in alignment with the bore of the body and having said elongate tubular member extending therethrough, a split ring collet encircling said resilient insert and a grip ring slidably mounted on said body and engaging said collet to cause the resilient insert to move into a position to prevent longitudinal movement of the elongate tubular member with respect to the insert and into a position permitting longitudinal movement of the elongate tubular member with respect to the insert.

6. A cannula as in claim 5 wherein said grip ring is mounted so that it is movable in a direction towards and away from the body and being movable by the fingers of the same hand engaging the cannula.

* * * * *